United States Patent
Chudoba et al.

[11] Patent Number: 6,077,430
[45] Date of Patent: Jun. 20, 2000

[54] METHOD FOR ELIMINATING PHOSPHOROUS CONTAINED IN EFFLUENTS

[75] Inventors: Pavel Chudoba, Le Peco; Roger Pujol, Chatou, both of France

[73] Assignee: Degremont, Rueil-Malmaison, France

[21] Appl. No.: 09/308,891

[22] PCT Filed: Oct. 20, 1997

[86] PCT No.: PCT/FR97/01877

§ 371 Date: May 26, 1999

§ 102(e) Date: May 26, 1999

[87] PCT Pub. No.: WO98/23542

PCT Pub. Date: Jun. 4, 1998

[30] Foreign Application Priority Data

Nov. 28, 1996 [FR] France .................................. 96 14609

[51] Int. Cl.[7] .................. C02F 3/30; C02F 3/12; C02F 3/00
[52] U.S. Cl. .................. 210/605; 210/614; 210/625; 210/631; 210/906
[58] Field of Search .................... 210/605, 614, 210/622–631, 906

[56] References Cited

U.S. PATENT DOCUMENTS

| | | | |
|---|---|---|---|
| 4,160,724 | 7/1979 | Laughton | 210/605 |
| 4,488,967 | 12/1984 | Block et al. | 210/605 |
| 4,948,510 | 8/1990 | Todd et al. | 210/605 |
| 5,076,928 | 12/1991 | Ballnus | 210/605 |
| 5,288,405 | 2/1994 | Lamb, III | 210/605 |
| 5,798,043 | 8/1998 | Khudenko | 210/605 |

FOREIGN PATENT DOCUMENTS

| | | |
|---|---|---|
| 2218180 | 11/1972 | Germany. |
| 3902626 | 8/1990 | Germany. |
| 4133805 | 5/1993 | Germany. |

*Primary Examiner*—Thomas G. Wyse
*Attorney, Agent, or Firm*—Pollock, Vande Sande & Amernick

[57] ABSTRACT

This method measures the soluble phosphorus concentration in the treated water for at least two different places of the treatment line: at the intake of the secondary clarification step to obtain a measurement P1 and at the outlet of the treatment line to obtain a measurement P2, the measurement P1 determining the amounts of the product precipitating the phosphorus in the liquor of at least one of the tanks in which the anoxic or aerobic steps are carried out upstream of the secondary clarification. The measurement P2 is continuously compared to the measurement P1 so as to detect a possible salting out of the phosphorus at the level of the secondary clarification. When the difference between these two measurements (ΔP1−P2) is noted, one of the two following measures occurs: supplementary injection of the precipitating product, before the secondary clarification, or modification of the flow rate of recirculation of the sludge of the clarification step towards the first anaerobic step.

9 Claims, 2 Drawing Sheets

ANAEROBIC STEP

AEROBIC STEP (ANOXIC)

METHOD FOR ELIMINATING PHOSPHOROUS CONTAINED IN EFFLUENTS

FIELD OF THE INVENTION

The present invention relates to optimized control of processes for the simultaneous removal, by the biological route and physicochemical route, of the phosphorus present in effluents, in particular sewage.

BAKGROUND OF THE INVENTION

The principle of biological dephosphatation is based on the ability of certain bacteria, known as poly-P bacteria, to accumulate phosphorus in the unstable form of polyphosphate complexes or of adenosine triphosphate (ATP). This accumulation takes place under aerobic or anoxic conditions, in the presence of dissolved oxygen or of nitrates. This aerobic accumulation is preceded by an upstream anaerobic stage, during which stage the poly-P bacteria carry out an anaerobic fermentation on the organic matter resulting from the sewage, in order to convert it into readily assimilable molecules: volatile fatty acids (VFA). These volatile fatty acids are subsequently converted by the poly-P bacteria into storage materials, known as poly-β-hydroxyalkanoates (PHA). The compound generally linked to these conversions is poly-β-hydroxybutyrate (PHB). In carrying out this conversion, the poly-P bacteria draw energy from the depolymerization of the intracellular polyphosphate stores. This process is accompanied by the release of soluble phosphorus, in the form of orthophosphates, into the medium. The return to aerobic or anoxic conditions is accompanied by the reverse process. The poly-P bacteria accumulate soluble phosphorus in the form of intracellular polyphosphates (ATP), using the PHB accumulated previously as energy source. This process is accompanied by disappearance of phosphorus from the soluble phase.

The mechanisms involved during the anaerobic phase (FIG. 1a) and aerobic phase (anoxic phase—FIG. 1b) have been summarized in the diagram of FIGS. 1a and 1b in the appended drawings.

Two possible configurations of the pathway employing biological dephosphatation have been illustrated, as non-limiting examples, in FIGS. 2a and 2b in the appended drawings. These configurations comprise a sequence of anaerobic 1, anoxic 2 and aerobic 3 regions (FIG. 2a) or anaerobic 1 and aerobic 3 regions (FIG. 2b). In addition, the pathway comprises a clarifier 4 (secondary clarifier), the function of which is to separate the biological sludge from the treated effluent, it being understood that this plant comprises, upstream of the regions 1, 2 and 3, conventional means for degritting, degreasing and optionally primary clarification. A portion of the sludge originating from the clarifier 4 is recycled at the head to the anaerobic region 1, the remainder going to bleed-off.

An example of a biological dephosphatation process is disclosed in German Patent document DE-A-3,902,626. In this publication, soluble organic compounds (organic carbon) are added to the water to be treated and the turbidity of the water and the phosphate content are measured at a single point, in the aeration tank, after separation of the sludge, and, by virtue of the two measurements thus obtained, the supply of air is regulated in the aeration step, as is the addition of acetic acid. The object of this known process is to accelerate biological dephosphatation and more particularly denitrification. It is mentioned in this prior publication that dephosphatation by the physicochemical route (addition of reagents precipitating phosphorus) constitutes a disadvantage.

Experience shows that, in practice, this process is often difficult to control as the forms of phosphorus accumulated within the bacterial cells are very unstable. A relatively short residence time in an anaerobic medium is sufficient for release of phosphorus into the soluble phase to take place.

The lack of reliability of processes employing a biological dephosphatation is often due to two main factors:
 unavailability or insufficiency of the source of readily assimilable carbon, which is reflected by a fraction which is too low and often variable over time of the readily assimilable COD in the sewage;
 uncontrolled release of phosphorus into the liquid phase during the prolonged residence times in the clarifier, which is reflected by operating problems.

These factors make it possible to explain the failures of conventional biological dephosphatation plants. In order to ensure a reliable level of treatment, biological dephosphatation and physicochemical dephosphatation are generally combined in the same pathway. The result is then known as combined dephosphatation.

A fraction of the phosphorus in the sewage is thus removed by the biological route, in the presence of the readily assimilable organic carbon of the sewage. The importance of this fraction of the phosphorus assimilated by the poly-P bacteria depends on the concentration of readily assimilable matter in the sewage. Thus, the contribution of the biological dephosphatation to the overall removal of phosphorus is highly variable, between 40 and 90%.

In order to ensure the efficiency of removal of phosphorus demanded by the required discharge level, the remainder of the phosphorus has to be removed by physicochemical precipitation. This precipitation generally takes place in the aeration region, following the injection of a precipitant, for example ferrous or ferric salts. The amount of the precipitant injected is calculated as a function of the concentration of phosphorus to be removed by precipitation, multiplied by a stoichiometric factor.

To date, the amount of the precipitant to be injected was estimated empirically or else the precipitant was injected in excess, in order to obtain complete removal of the phosphorus. The doses can sometimes be controlled by the measurement of the soluble phosphorus in the sewage at the inlet of the plant.

However, these methods of injection cannot guarantee, in a reliable way, the sometimes very strict discharge level of phosphorus-comprising matter. When precipitation of the phosphorus is combined with biological dephosphatation mechanisms, the fractions of the phosphorus incorporated by the poly-P bacteria are always in a highly unstable state. A problem in the secondary clarification, an operating fault or very simply a malfunction of some items of equipment is then sufficient for release of phosphorus into the liquid phase during clarification to take place. This results in an immediate deterioration in the discharge level of phosphorus-comprising matter and in discharge standards not being observed.

BRIEF DESCRIPTION OF THE INVENTION

In order to mitigate the disadvantages of the solutions according to the prior art, which solutions are recalled above, the present invention introduces a process for the treatment of sewage simultaneously by the biological route and the physicochemical route which employs biological dephosphatation, this process comprising stages of anaerobic, anoxic and aerobic treatments, followed by a stage of secondary clarification, the sewage being mixed with the biological sludge recycled from the secondary clarification stage in the first anaerobic stage, in order to bring about release of phosphorus into the soluble phase by the poly-P bacteria, the said mixture subsequently being subjected to the conventional stages of anoxic and aerobic treatments, the activated sludge being separated from the treated water in the secondary clarification stage and subsequently being partially recycled in the anaerobic stage, at the head of the treatment line, and partially extracted from the system, this process being characterized in that:

the concentration of soluble phosphorus in the treated water is measured at at least two different points on the treatment line: at the inlet of the secondary clarification stage, in order to obtain a measurement P1, and at the outlet of the treatment line, in order to obtain a measurement P2, the measurement P1 determining the doses of the product which precipitates soluble phosphorus by the physicochemical route which have to be injected into the liquor of at least one of the tanks where the anoxic or aerobic stages are carried out upstream of the secondary clarification;

the measurement P2 is continuously compared with the measurement P1, in order to detect possible release of phosphorus in the secondary clarification, and, when the difference in the two measurements ($\Delta P1-P2$) is found, at least one of the two following measures is triggered:

an additional injection of the precipitant is carried out before the secondary clarification, in order for precipitation of the phosphorus released during the secondary clarification stage to be able to take place by virtue of the excess of the precipitant injected;

the flow rate for recirculation of the sludge from the clarification stage to the anaerobic first stage is modified in order to reduce its residence time during this clarification stage.

According to one characteristic of the present invention, the difference between the measurements P1 and P2 ($\Delta P1-P2$) which brings about the modification in the doses of the product which precipitates soluble phosphorus by the physicochemical route or the modification in the flow rate for recirculation of the sludge is between 0.1 and 2 mg of $P-PO_4/l$, preferably between 0.1 and 0.5 mg of $P-PO_4/l$.

DETAILED DESCRIPTION

In order to give a better understanding of the process which is the subject-matter of the present invention, an embodiment of it has been described below. Of course, it remains the case that this is only an example which does not have any limiting nature. During this description, reference is made to FIG. 3 of the appended drawings, which is a diagram illustrating the various stages of the process according to the invention.

Figure 1A:
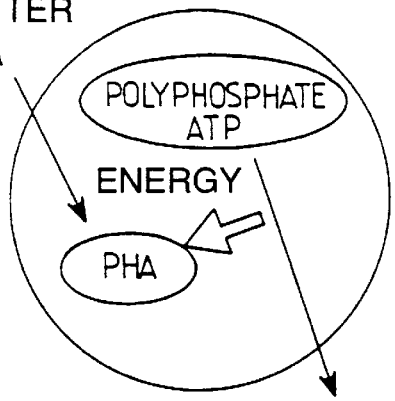
FIG. 1a illustrates the mechanisms involved during the anaerobic phase of the present invention.
Figure 1B:
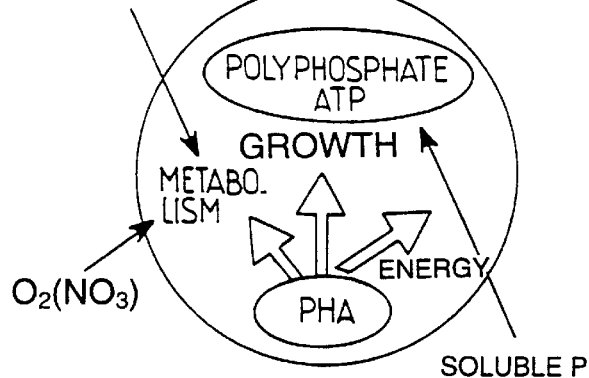
FIG. 1b illustrates the mechanisms involved during the aerobic phase of the present invention.
Figure 2A:
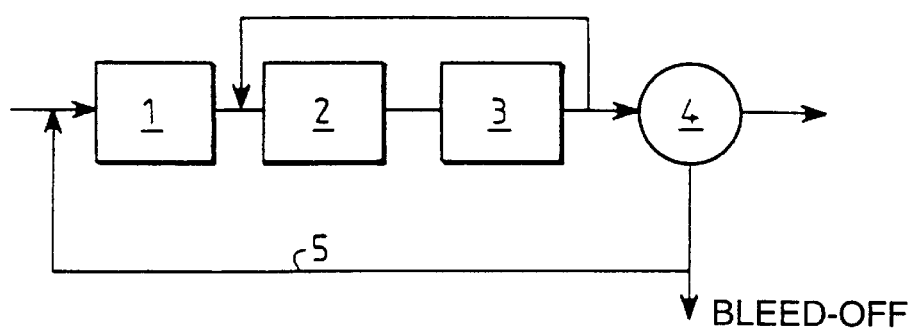
FIGS. 2a and 2b illustrate possible configurations of the pathway employing biological dephosphatation.
Figure 2B:
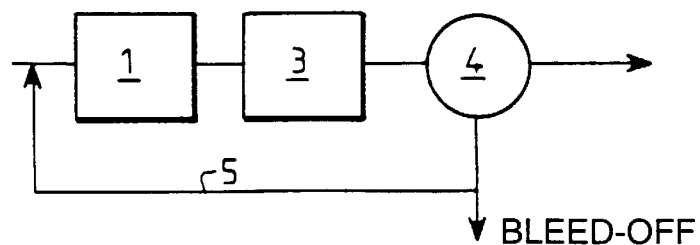
Figure 3:
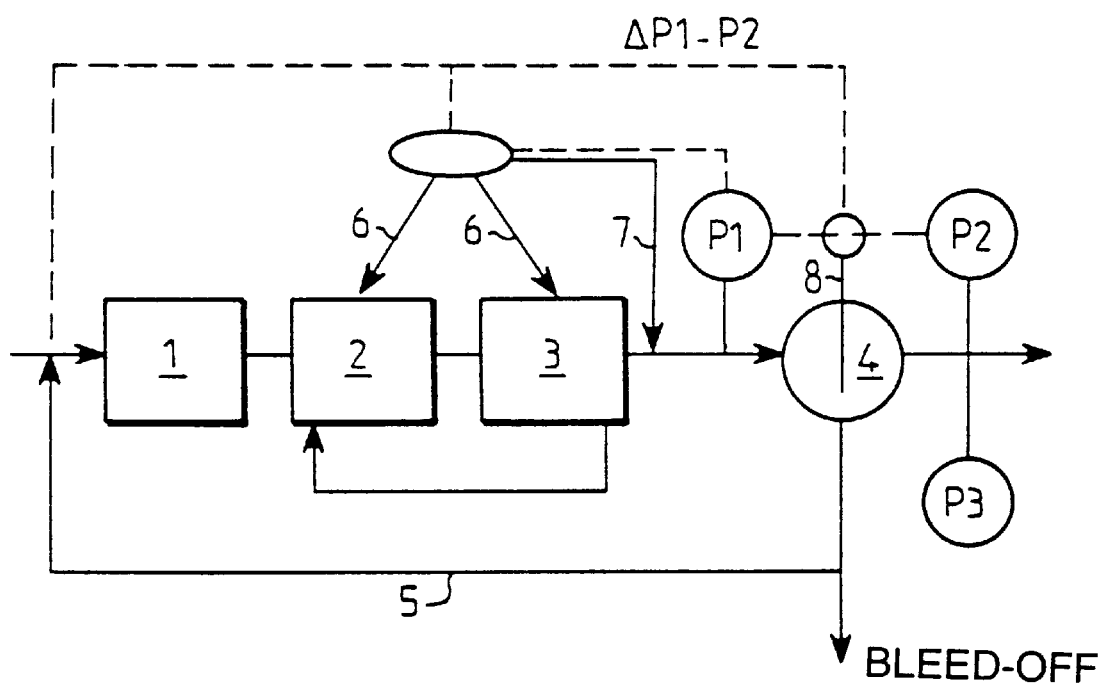
FIG. 3 is a block diagram of the present method.

The anaerobic region 1, the anoxic region 2 and the aerobic region 3 are reencountered in FIG. 3, as well as the secondary clarifier 4 from which a portion of the sludge 5 is recycled to the anaerobic stage 1. The secondary clarifier comprises, as known, a sludge bleed-off.

As is understood, the process which is the subject-matter of the present invention essentially comprises a measurement of the concentration of soluble phosphorus (ortho- or polyphosphates) at two points on the treatment line, namely upstream and downstream of the secondary clarifier (FIG. 3).

In FIG. 3, the first continuous measurement P1 determines the level of soluble phosphorus in the liquor exiting from the aerobic region 3 and governs the injections of the precipitant 6 into one of the preceding regions 2, 3 as required. This measurement P1 makes it possible to adjust the dose of the precipitant as a function of the value measured. The second continuous measurement P2 determines the level of soluble phosphorus at the outlet of the secondary clarifier 4, which corresponds to the discharge level, and this measurement is compared with the level detected by the measurement P1, so as to obtain a measurement of the difference ($\Delta P1-P2$). The object of the measurement P2 is above all to detect any anomaly leading to the release of phosphorus in the secondary clarifier 4.

According to the present invention, when the difference $\Delta P1-P2$ between the two measurements P1 and P2 exceeds a predetermined value, generally set between 0.1 and 2 mg of $P-PO_4/l$ and preferably between 0.1 and 0.5 mg of $P-PO_4/l$, two types of action can be triggered:

Firstly, the dose of the precipitant, initially determined by the measurement P1, can be supplemented by a second injection 7 of this precipitant carried out before the secondary clarification region 4, in order for precipitation of the phosphorus released in the clarifier to be able to take place by virtue of the excess of the precipitant injected. This secondary injection can be carried out continuously or batchwise in one of the regions preceding the secondary clarification 4 or at the inlet of the secondary clarification region. It can also be carried out at the same point as the first injection governed by the measurement P1.

A second action consists in acting directly on the sludge which is releasing the phosphorus by reducing its residence time in the secondary clarifier 4. This is carried out by virtue of an increase in the flow rate 5 for recirculation of the sludge. This action can be coupled with a measurement of the blanket level of the sludge 8.

Still according to the diagram of FIG. 3, the output level of the treated water is also controlled by a measurement P3 of the turbidity, in order to make it possible to detect possible losses of DM, which would result in an increase in the concentration of particulate phosphorus in the discharge.

According to the present invention, the measurements of the concentration of soluble phosphorus in the treated water, P1 and P2, can be obtained either from two different measurement devices or from a single device with two sampling points.

It will be remembered from the preceding description that the process which is the subject-matter of the present invention is clearly distinguished from the prior state of the art recalled above (DE-3,902,626), in particular in that it relates to the simultaneous treatment by the biological route and the physicochemical route, which is positively advised against in this prior state of the art. Furthermore, in the invention and in contrast to the prior state of the art, the aim is not to improve denitrification and consequently organic carbon is not added to the effluent to be treated.

The advantages of the process which is the subject-matter of the present invention, with respect to the prior state of the dephosphatation art, are in particular as follows:

- continuous detection of any anomaly or of any failure as regards release of phosphorus in the clarifier,
- control and better reliability of the discharge level of phosphorus,
- better control of the doses of the precipitant, which is reflected in savings,
- optimization of the combination of the biological and physicochemical dephosphatations.

Of course, it remains that the present invention is not limited to the implementational examples described and/or represented but that it encompasses all the alternative forms thereof.

What is claimed is:

1. Process for the treatment of sewage by a biological route and a physicochemical route which employs biological dephosphatation, this process comprising stages of anaerobic, anoxic and aerobic treatments, followed by a stage of secondary clarification, the sewage being mixed with biological sludge recycled from the secondary clarification stage in a first anaerobic stage, in order to bring about release of phosphorus into a soluble phase by the poly-P bacteria, the mixture subsequently being subjected to the conventional stages of anoxic and aerobic treatments, activated sludge being separated from the treated water in the secondary clarification stage and subsequently being partially recycled in the anaerobic stage, at the head of a treatment line, and partially extracted from the system wherein:

- the concentration of soluble phosphorus in the treated water is measured at at least two different points on the treatment line: at the inlet of the secondary clarification stage, in order to obtain a measurement P1, and at the outlet of the treatment line, in order to obtain a measurement P2, the measurement P1 determining the doses of the product which precipitates soluble phosphorus by the physicochemical route in the liquor of at least one of the tanks where the anoxic or aerobic stages are carried out upstream of the secondary clarification;
- the measurement P2 is continuously compared with the measurement P1, in order to detect possible release of phosphorus in the secondary clarification; and
- when the difference in the two measurements ($\Delta$P1–P2) is found, at least one of the two following measures is triggered:
  - an additional injection of precipitation is carried out before the secondary clarification, in order for precipitation of the phosphorus released during the secondary clarification stage to be able to take place by virtue of the excess of the precipitant injected;
  - the flow rate for recirculation of the sludge from the clarification stage to the anaerobic first stage is modified in order to reduce its residence time during the clarification stage.

2. The process according to claim 1, wherein the injections of the product which precipitates soluble phosphorus by the physicochemical route are carried out continuously during one of the stages preceding the clarification.

3. The process according to claim 1, wherein the injections of the product which precipitates soluble phosphorus by the physicochemical route are carried out batchwise during one of the stages preceding the clarification.

4. The process according to claim 1 further comprising the step of measuring continuously the turbidity of the final effluent.

5. The process according to claim 1 wherein the additional injection of the product which precipitates phosphorus in the soluble phase by the physicochemical route is carried out at the same point as the injection governed by the measurement P1.

6. The process according to claim 1, wherein the additional injection of the product which precipitates phosphorus in the soluble phase by the physicochemical route is carried out at the inlet of the clarification stage.

7. The process according to claim 1, wherein the difference between the measurements P1 and P2 ($\Delta$P1–P2) which leads to the modification in the doses of the product which precipitates soluble phosphorus by the physicochemical route or the modification in the flow rate for recirculation of the sludge lies in the range from 0.1 to 2 mg of P-PO$_4$/l, preferably in the range of 0.1–0.5 P-PO$_4$/l.

8. The process according to claim 1, wherein the measurements of the concentration of soluble phosphorus, P1 and P2, are provided by two different devices.

9. The process according to claim 1, wherein the measurements of the concentration of soluble phosphorus, P1 and P2, are provided by one device with two sampling points.

* * * * *